United States Patent [19]
Meller

[11] Patent Number: 5,232,363
[45] Date of Patent: Aug. 3, 1993

[54] SCALER WITH IMPROVED VIBRATION CHARACTERISTICS

[75] Inventor: Moshe Meller, Lakewood, N.J.

[73] Assignee: Eran Meller, Haifa, Israel

[21] Appl. No.: 911,251

[22] Filed: Jul. 7, 1992

Related U.S. Application Data

[63] Continuation of Ser. No. 714,146, Jun. 11, 1991.

[51] Int. Cl.$^5$ ................................................ A61C 1/08
[52] U.S. Cl. ..................................... 433/117; 433/120
[58] Field of Search ............... 433/117, 118, 119, 120, 433/132

[56] References Cited

U.S. PATENT DOCUMENTS

| | | | |
|---|---|---|---|
| Re. 30,536 | 3/1981 | Perdreaux, Jr. ................. | 433/119 X |
| 3,811,190 | 5/1974 | Sertich ................................ | 433/118 |
| 4,203,221 | 5/1980 | Knopp et al. ..................... | 433/117 |
| 4,260,380 | 4/1981 | Nash .................................... | 433/119 |
| 4,330,282 | 5/1982 | Nash .................................... | 433/118 |
| 4,484,893 | 11/1984 | Finn .................................... | 433/118 |
| 4,589,847 | 5/1986 | Loge et al. ....................... | 433/118 X |

*Primary Examiner*—Gene M. Mancene
*Assistant Examiner*—Nicholas D. Lucchesi
*Attorney, Agent, or Firm*—Frishauf, Holtz, Goodman & Woodward

[57] ABSTRACT

A dental scaler comprises an elongated housing having a forward end at which a dental scaling tool is removably connectable, and a rearward end for connection to a source of pressure working fluid. A substantially rigid elongated tubular member is resiliently supported in the housing. A vibration imparting device is coupled to an intermediate portion of the elongated tubular member, and is driven by the pressure working fluid to vibrate the elongated tubular member. A dental scaling tool is connected at the forward end portion of the elongated tubular member, and is vibrated by the vibrations produced by the vibration device. A frequency stabilizing weight is fixedly and immovably secured to a rearward end portion of the elongated tubular member for stabilizing the frequency of the vibration imparted to the forward end portion of the elongated tubular member, the weight having an outer dimension smaller than the inner dimension of the housing in the vicinity of the weight so as not to contact the housing during vibration of the elongated tubular member. The weight is preferably substantially disk-shaped, and is preferably arranged close to the rear end of the elongated tubular member. An anti-rotation device may be coupled to a forward end portion of the elongated tubular member for preventing rotation thereof relative to the housing.

14 Claims, 3 Drawing Sheets

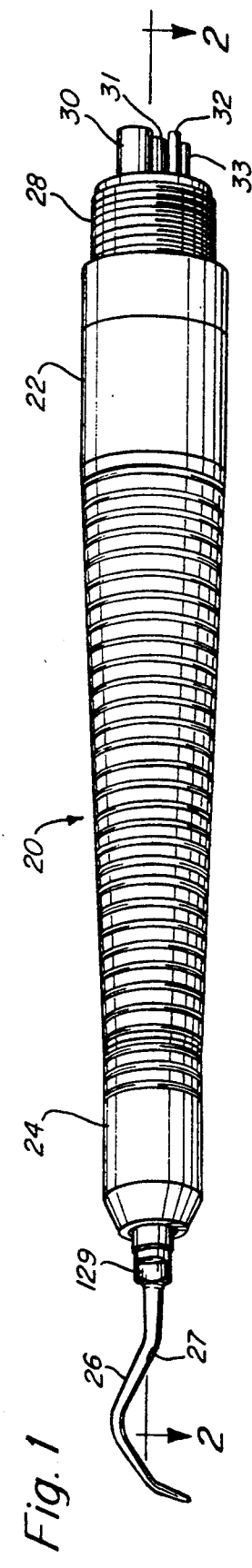
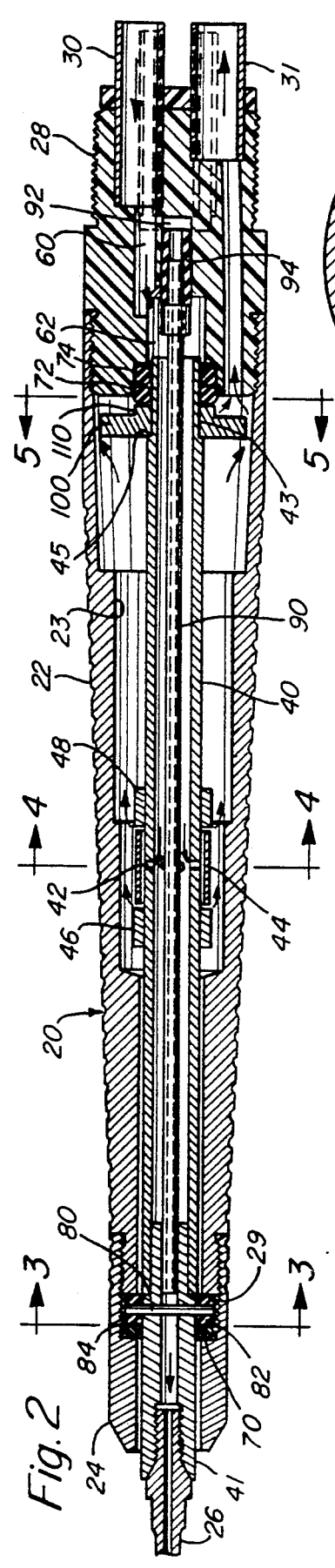
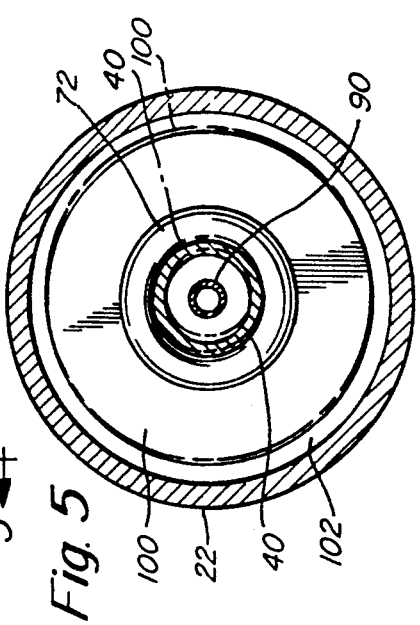
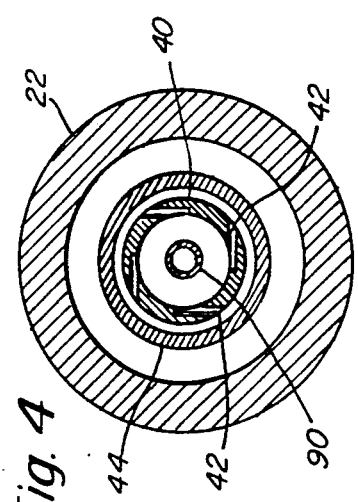
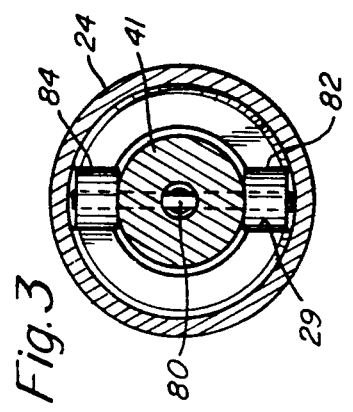

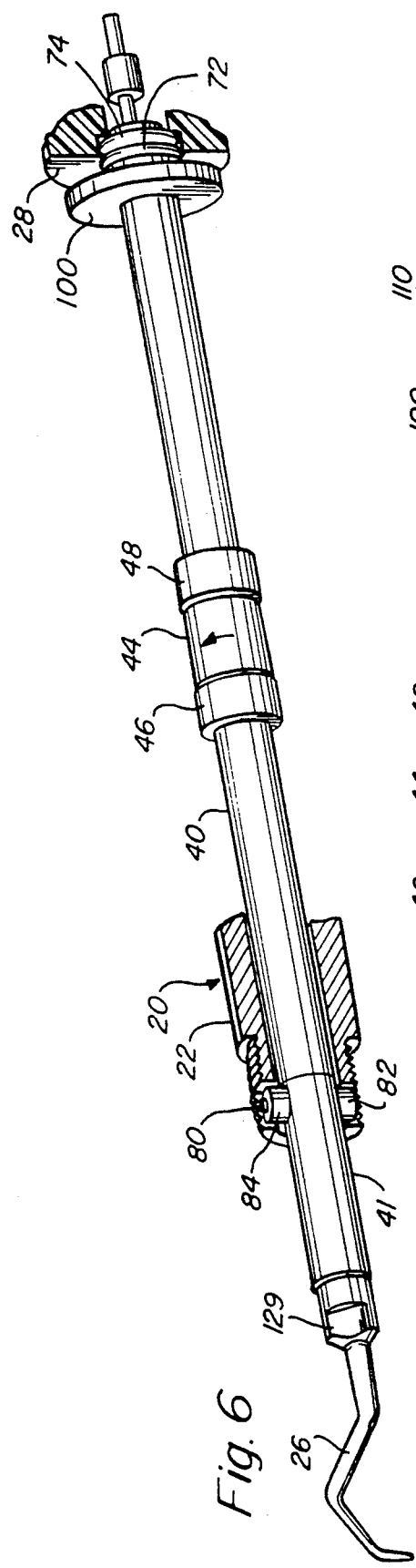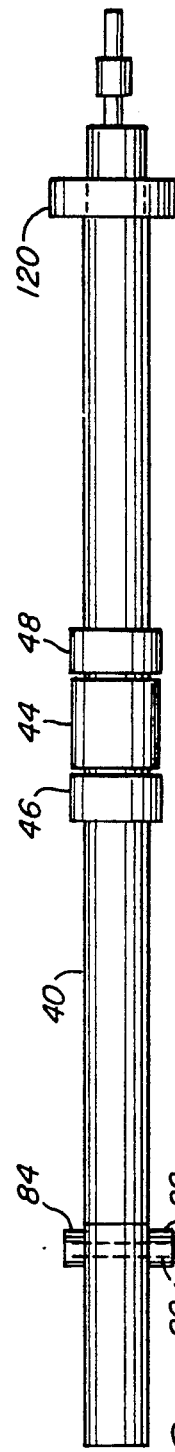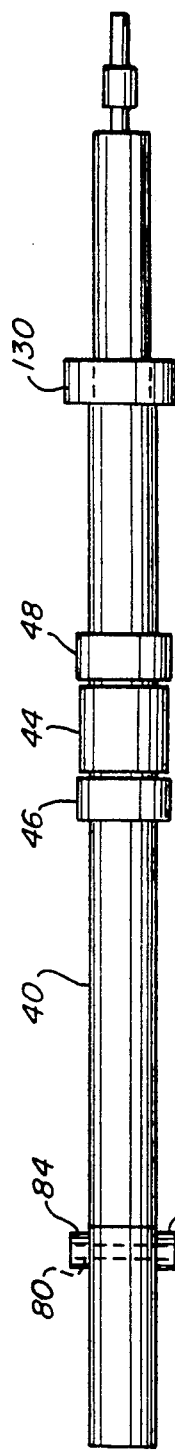

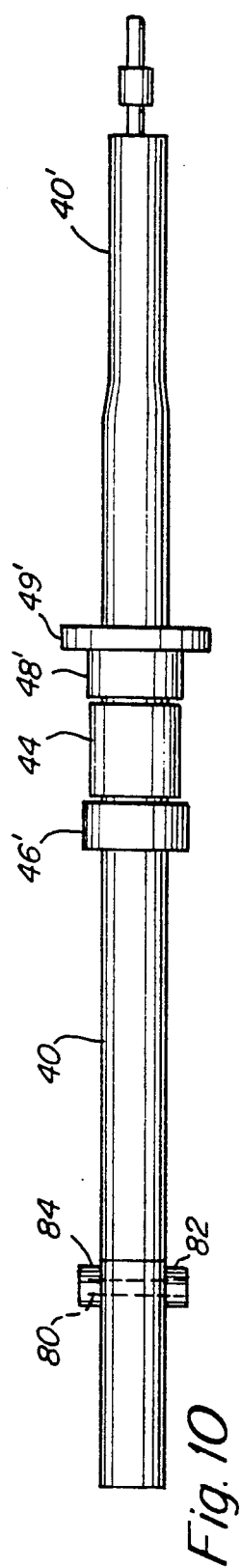

SCALER WITH IMPROVED VIBRATION CHARACTERISTICS

This application is a continuation of application Ser. No. 07/714,146, filed Jun. 11, 1991.

BACKGROUND OF THE INVENTION

This invention relates to an air-driven scaler, and more particularly to an air-driven dental tooth scaler having improved vibration characteristics. The invention also relates to such a scaler having general industrial rise, such as for use in polishing hard metals, or the like.

While the invention is applicable to uses other than as a dental scaler, the following discussion and detailed description is given with respect to dental tooth scalers by way of example, it being clear that the device is equally applicable for other uses where a vibrating tip is required, such as for polishing hard metals when making molds for injection molding or other molds, and for other uses.

Air-driven vibrating-type dental tooth scalers are known in the art, for example as disclosed in U.S. Pat. No. 3,811,190, U.S. Pat. No. 4,330,282 and others. However, the known air-driven dental scalers have unstable or undesirable vibration frequency characteristics, and have frequencies of vibration which vary widely during application of a load during use, and depending upon the type of scaling tool connected to the working end thereof.

It is the object of the present invention to provide an improved air-driven dental scaler which has stable vibration frequency characteristics, even during use and over a wide range of applied loads, and in which the vibration frequency is stable at an optimum frequency for use as a dental scaler.

A further object of the invention is to provide such an improved air-driven dental scaler which is relatively simple in construction and which involves only relatively small modifications to the known air-driven vibration-imparting mechanism.

SUMMARY OF THE INVENTION

According to the present invention, a dental scaler comprises an elongated housing having a forward end at which a working tool is removably connectable, and a rearward end including means for connection to a source of pressure working fluid; a substantially rigid elongated tubular member resiliently supported in said housing, said elongated tubular member having forward and rearward end portions; vibration means coupled to a portion of said elongated tubular member intermediate said forward and rearward end portions thereof, and driven by said pressure working fluid to vibrate said elongated tubular member; and means at said forward end portion of said elongated tubular member for connecting a dental scaling tool thereto, said forward end portion of said elongated tubular member being vibrated by said vibration means to thereby impart vibration to said dental scaling tool. Further provided is a weight member fixedly and immovably secured to a rearward end portion of said elongated tubular member for stabilizing the frequency of the vibration imparted to said forward end portion of said elongated tubular member, said weight member having an outer dimension smaller than the inner dimension of said housing in the vicinity of said weight member so as not to contact said housing during vibration of said elongated tubular member and of said weight member.

The weight member is preferably substantially disk-shaped, and is preferably arranged close to the rear end of the elongated tubular member.

According to another feature of the invention, the dental scaler comprises anti-rotation means coupled to a forward end portion of said elongated tubular member for preventing rotation of the elongated tubular member relative to the housing. The anti-rotation means preferably comprises an elongated member passing through an opening in a forward end portion of the elongated tubular member and resiliently connected to the housing at the opposite ends of the elongated anti-rotation member.

According to another aspect of the invention, the vibration-type scaler described above can be used to polish hard metals, such as when making molds for injection molding machines, and the like.

BRIEF DESCRIPTION OF THE DRAWINGS

FIG. 1 is a perspective view of a dental scaler to which the present invention pertains;

FIG. 2 is a section taken along line 2—2 in FIG. 1;

FIG. 3 is a section taken along line 3—3 in FIG. 2, showing the forward end in detail;

FIG. 4 is a section taken along line 4—4 in FIG. 2, showing the air-driven vibration imparting mechanism;

FIG. 5 is a section taken along line 5—5 in FIG. 2, showing the improved frequency stabilization technique of the present invention;

FIG. 6 is a partly broken away perspective view of the internal mechanism of the dental scaler of the present invention;

FIG. 7 is a side view of the internal vibration imparting mechanism of the present invention, which is shown in FIGS. 2 and 6;

FIG. 8 is a side view of a modified embodiment of the vibration stabilization mechanism of the present invention;

FIG. 9 is a side view of another modified embodiment of the vibration stabilization mechanism of the present invention; and FIG. 10 is a side view of still another modified embodiment of the vibration stabilization mechanism of the present invention.

DETAILED DESCRIPTION

FIG. 1 shows a perspective outer view of a dental scaler 20 of the present invention. The dental scaler comprises an outer housing 22 having a removable forward tip 24 and a scaling tip or working tool 26 coupled to the front or forward end of the scaler. The rear end of the scaler has a threaded coupling 28 which is adapted to be connected to the air and water supply tube of an ordinary dental work station, and has tubes 30, 31, 32 and 33, which are conventional, extending rearwardly thereof. The tubes 30-33 will be described hereinbelow.

From the outside, the dental scaler of the present invention, shown in FIG. 1, looks substantially similar to an ordinary dental scaler. The scaling tip 26 has a water outlet hole 27 therein, which is conventional.

FIG. 2 illustrates the internal mechanism of the dental scaler of the present invention in detail. The discussion of FIG. 2 can be more easily understood when read in conjunction with FIGS. 3, 4, 5 and 6. Internally of the outer housing 22 is mounted an elongated, and substantially rigid, tubular beam member 40 having an air passage therethrough. See FIG. 6. The tubular beam member 40, at an intermediate portion thereof, has tangentially or angularly directed openings or ports 42 therein, and around which is mounted loosely a rotor 44 which is rotatable on the beam member 42. Air is supplied internally of member 40 via the tube 30 from a compressed air supply source (not shown) through an internal passage 60 of threaded coupling member 28, through another internal space 62, and then through the interior of the elongated tubular beam member 40, and out through the angularly oriented openings, holes or ports 42 to cause the rotor 44 to rotate and vibrate on the rigid elongated beam member 40. The air flow path is shown by arrows in FIG. 2. The operation of the air-driven rotor 44, as described above, is substantially the same as is shown in U.S. Pat. No. 4,330,282, the entire contents of which is incorporated herein by reference. Fixed metallic bush members 46, 48 are press-fit on the outer surface of elongated member 40 to retain the rotor 44 in axial position while permitting rotation of the rotor. Exhaust air is exhausted outwardly from the rear device as shown by the arrows directed from left-to-right in FIG. 2, and out through tube 31.

The elongated tubular beam member 40 is suspended within the apparatus by means of resilient elastomeric suspension members at the forward and rear ends thereof. At the forward end is an O-ring 70, and at the rearward end is a pair of O-rings 72, 74. These O-rings resiliently suspend the vibrating tubular elongated member 40 within the outer housing 22.

The forward end of the device comprises a transverse pin 80 which passes through the forward tubular portion 41 which is connected to the forward tubular end portion of beam member 40 to serve as an extension thereof. The pin 80 passes through openings in forward member 41 as shown in FIGS. 2 and 3, and is suspended at its opposite ends in resilient elastomeric rings or blocks 82, 84, as seen in FIGS. 2 and 3. The forward end portion of outer housing 22 has a longitudinal slot 29 therein which receives the elastomeric members 82, 84 for retaining the pin 80 in fixed, non-rotational position at the forward end of the device, as seen in FIGS. 2, 3 and 6. The purpose of pin 80 and the O-ring seal 70 is to prevent rotation of the main beam or tubular member 40 relative to the outer housing 20 during tightening and releasing of the forward portion 24 during releasing and/or replacing of the working tip or tool 26. The working tip 26 is replaced in a conventional manner by unscrewing same from the forward end of internally threaded connector member 41, by means of, for example, engaging a tool on the side flats 129 of the working tip 26, which flats are shown clearly in FIGS. 1 and 6. It has been found that it is important to maintain the elongated beam or tubular member 40 non-rotational during replacing or releasing of the working tip 26, and during operation of the device. The resilient mounting members 82, 84 and forward O-ring 70 provides sufficient resiliency to enable the transverse anti-rotation pin 80 to be provided without adversely affecting the vibrational characteristics of the overall device.

Internally of the tubular member or beam 40 is a water conduit 90 which extends from a water manifold 92 at the rear end of the device, which water conduit 90 is sealed in the threaded member 28 by means of an elastomeric press-fit seal 94. Water, supplied by the dental unit through one of the inlet tubes 32, 33, passes through internal passageways in the threaded member 28 to the manifold 92, and then through the internal bore of the conduit 90, and out through the water outlet opening 27 in the working tip 26, as shown by the arrow at the forward-most portion of the device in FIG. 2.

As best seen in FIGS. 2, 5, 6 and 7, the main feature of the present invention is the provision of a weight or balancing disk 100 at the rear end portion of the elongated tubular beam member 40. The weight or balancing disk or member 100 is placed rearwardly of the rotor 42, as shown in the drawings. As seen in FIG. 2, in a first embodiment of the invention, the weight disk 100 is fixedly connected to the rear end portion of the tubular member or beam 40, for example by means of a press-fit and/or by means of an adhesive, such as an epoxy or other suitable adhesive for connecting metallic members together. Preferably, the weight member 100 is made from brass as is the tubular elongated beam member 40. The tubular beam 40 has a necked-down rear end portion 43 having a reduced outer diameter so as to define a stop or abutment wall 45 against which said weight 100 can abut for firmer engagement and retention on the elongated tubular beam member 40. The weight disk 100 is designed so as to have a smaller outer diameter then the inner diameter of the housing 22 in the vicinity in which it is placed. This is to permit vibration of the weight 100 without the weight member 100 contacting or abutting the inner surface of the outer housing 22, and to also permit at least exhaust air flow out of the rear of the device around the outer peripheral surface of the weight disk 100, as shown by the arrows in the vicinity of the weight 100 in FIG. 2. FIG. 5 shows the space 102 between the outer periphery of the weight 100 and the inner peripheral surface of the housing portion 22. The vibration or oscillating motion of the weight 100 is shown in phantom lines in FIG. 5 for the purpose of illustration.

The resiliency of the O-rings 72, 74 is sufficient to retain the vibrating beam 40 in position, and to also permit vibration thereof. The O-rings 72, 74 and 70 are conventional O-rings made of elastomeric materials. Such O-rings are well known in the art and are disclosed, for example, in U.S. Pat. No. 4,330,282. Similarly, elastomeric suspension materials are shown in U.S. Pat. No. 3,811,190. Therefore, a further detailed discussion of the elastomeric O-rings or the like shown herein is deemed unnecessary.

Preferably, the weight member 100 is a substantially flat, relatively large-diameter, disk-shaped member which has a diameter substantially greater than its thickness, as shown in FIGS. 2, 6 and 7. As shown in FIGS. 2 and 7, the rearward directed portion of the weight member 100 has a reduced diameter shoulder portion 110 which bears against the forward-most O-ring 72. The shoulder portion 110 provides a greater surface engagement with the tubular beam 40 for better retention thereon, and also provides a bearing surface for bearing against the O-ring 72 without adversely affecting the vibration characteristics.

The weight 100 is designed to provide a concentrated weight over a small length of the elongated tubular beam 40. However, the weight may be made with a smaller diameter and a greater thickness, as shown by weight 120 in FIG. 8. While this design of FIG. 8 will provide the desired effect, the effects provided by the weight arrangement of FIGS. 2, 6 and 7, are, at this time, considered preferable.

While the weight is shown at the rearward end of the tubular beam 40 in FIGS. 7 and 8, the weight could be moved forwardly, as shown by weight 130 in FIG. 9. The weight 130 in FIG. 9 is shown relatively reduced in diameter as compared to the weights 100 and 120 of FIGS. 7 and 8, respectively. This is because the weight 130 is arranged so as to be within the reduced diameter portion 23 of outer housing 22. If the inner diameter 23 of the outer housing 22 is increased, then, of course, the outer diameter of the weight 130 could be correspondingly increased. In all cases, the weights of FIGS. 6–9 are dimensioned so as to provide sufficient space between the outer peripheral surface thereof and the inner peripheral surface of the outer housing 22, so that the weights do not contact the inner surface of the outer housing 22 during vibration operation.

In all of the above-described embodiments, the weights or balancing (or stabilizing) disks 100, 120 and 130 can be press-fit and/or adhered to the elongated beam 40 by means of an adhesive or glue. A particularly suitable adhesive is LOCTITE (registered trademark). Alternatively, instead of making the weights 100, 120, 130 as separate members and adhering them or press-fitting them onto the beam 40, the weights 100, 120, 130 could be integrally formed or machined with beam 40 as one integral, unitary piece. Such machining can be carried out on a lathe, or other suitable machine tool during production. The appearance of integrally machined units would be substantially the same as those shown in FIGS. 7–9.

FIG. 10 shows another embodiment of the invention wherein one or both of the ring members 46,, 48, on opposite sides of vibrating ring 44 are enlarged and/or widened to increase their respective masses so as to serve as a respective stabilizing weight or disk, in replacement for any of the weights or disks 100, 120, 130 previously described with respect to FIGS. 7–9. Depending upon the desired vibration characteristics, and the weights and sizes of the over-sized ring members 46', 48', the desired frequency of vibration can be obtained and stabilized. It should be clear that only one of ring members 46', 48' may be enlarged and/or widened, or both could be enlarged and/or widened, depending upon the relative sizes, characteristics, internal diameter of the housing 22, overall dimensions of the device, etc. The enlarged ring members 46', 48, are press-fit on the beam 40 in the conventional manner, and/or may be adhered thereto. Still further, one of the fixed ring members 46', 48' can be integrally machined with the beam 40 to form a unitary unit, as described above, for example by means of a lathe. While the effect with enlarged (and/or widened) members 46' and/or 48' may not be as prominent as the effects obtained with above-described balancing or stabilizing weights 100 120, 130, an improved effect can be obtained by the arrangement of FIG. 10 as compared to the prior art devices. As should be clear from the drawings, especially FIG. 2, the limitation on the outer diameter of the fixed rings 46', 48' is the inner diameter of the corresponding portion of the outer housing 22. As shown in FIG. 10, the forward-most ring 46' is only slightly enlarged in outer diameter so as to still fit within the inner diameter of the housing 22, without contacting same. The rearward ring 48' is shown in FIG. 10 as having a widened or elongated axial portion with a stepped outer enlarged diameter portion 49' which has an outer diameter so as not to contact the corresponding inner diameter portion of housing 22. The degree of axial elongation of the members 46', 48', and the degree of enlargement of the outer diameters thereof, depends upon particular system applications.

While the rearward portion 40' of the beam 40 is shown as having a reduced outer diameter, the outer diameter of the rearward portion 40' can be the same as the outer diameter of the forward portion of the beam 40, as desired.

In use, it is desired that the vibration frequency of the working tip 26 be at around 2000 to 3000 Hz, preferably around 2500 Hz for best operation of the scaler, for the optimum useful life of the working tool, and for the best operational characteristics (that is, reduced noise, comfortable handling, etc.). It has been found that the provision of the weights 100 (and 120, 130) at the rearward portions of the device, rearward of the rotor 42, provides the optimum desired frequency of about 2500 Hz. The precise reason why the weight of the present invention provides the vast improvement over the prior art devices is not fully understood. However, it is believed that the weight 100 (and 120, 130) effectively lengthens the tubular beam 40 and results in a lower frequency standing wave. In use as a scaler, the vibration frequency remains substantially stable, and drops only by about 100–200 Hz. This stability of vibration frequency is very desirable.

In the prior art devices, without the free weights at the rear end portions of the vibrating beam, the working frequency was up to about 6000 Hz, which is undesirable. Such a high working frequency reduced the life of the working tool or tip 26 and the internal working parts of the device. Also, the very high frequency of 6000 Hz resulted in lower cleaning efficiency of calculus or plaque from the teeth, and provided a noisier device. The present invention, which operates stably at around 2500 Hz, provides improved longer life of the working tip and internal working parts of the mechanism, higher cleaning efficiency and quieter operation, thereby making the device not only more comfortable for use in the patient's mouth, but also more comfortable for the practitioner, and provides less trauma (less noise) to the patient.

The O-ring seals at the forward and rear ends of the device prevent intrusion of contamination, maintain cleanliness of the internal working members, and do not adversely affect the vibration characteristics of the device.

A detailed discussion of the operation of the rotor 44 and how it imparts vibration to the apparatus is, as mentioned above, described in detail in U.S. Pat. Nos. 3,811,190 and 4,330,282, the entire contents of which are incorporated herein by reference. The present invention utilizes this basic vibration imparting device. In the present invention, the tubular member or beam 40 is preferably made of brass, which is easily machined and worked. The various other metallic members of the device are also preferably made of brass. However, it is clear that other materials such as stainless steel or other suitable metals, and or even some plastic materials, could be used, as desired. In the embodiment of FIG. 9, the weight is shown approximately one-third along the beam 40, as measured from the rear end portion thereof. This position is not limiting, but is given only by way of example, as should be clear from FIG. 10.

In a preferred embodiment, the length of the elongated tubular beam member 40 is approximately 95 mm (about 3¾ inches), and the mass of the weight member 100 may range from about 1 to 2 grams, and may be, for example, about 1.5 grams. It is to be understood that other lengths of elongated tubular members can be used, and other weights of the weights 100 can be used, depending upon overall system configuration, including size of device, types of materials used, weights of materials, dimensions, etc. The critical feature is the placement of the stabilizing weight 100 at the rear portion of the elongated tubular member (rearward of the vibration rotor 44), the weight being fixedly connected to the rear portion of the elongated tubular beam member 40 and being dimensioned so as never to contact the inner surface of the housing 22 during vibration of the system. Also, the rear end portion of the elongated tubular member must be resiliently supported to permit vibration thereof, such as by the O-rings 72, 74.

Having described a specific preferred embodiment of the invention with reference to the accompanying drawings, it will be appreciated that the present invention is not limited to that specific embodiment, and that various changes and modifications can be effected therein by one of ordinary skill in the art, and the various features can be used in any combination, without departing from the scope or spirit of the invention as defined in the appended claims.

What is claimed is:

1. A dental scaler comprising:
   an elongated housing having a forward end at which a working tool is removably connectable, and a rearward end including means for connection to a source of pressure working fluid;
   a substantially rigid elongated tubular member resiliently supported in said housing, said elongated tubular member having forward and rearward end portions;
   vibration means coupled to a portion of said elongated tubular member intermediate said forward and rearward end portions thereof, and driven by said pressure working fluid to vibrate said elongated tubular member, siaid vibration means including a rotor mounted on said elongated tubular member and two stop members on said elongated tubular member close to said rotor on respective opposite sides of said rotor for limiting movement of said rotor in the longitudinal direction of said elongated tubular member;
   means at said forward end portion of said elongated tubular member for connecting a dental scaling tool thereto, said forward end portion of said elongated tubular member being vibrated by said vibration means to thereby impart vibration to said dental scaling tool;
   a weight member, separate from and spaced apart from said vibration means, and fixedly and immovably secured directly to a rearward end portion of said elongated tubular member without any resilient material between said weight member and said elongated tubular member, for stabilizing the frequency of the vibration imparted to said forward end portion of said elongated tubular member, at least a peripheral portion of said weight member having a space on both its sides in an axial direction of said tubular member so as to render said weight member substantially freely vibratable with said elongated tubular member, said weight member being located close to the rear end of said elongated tubular member and intermediate the position of said vibration means and a rearward-most end of said elongated tubular member, and said weight member having an outer dimension smaller than the inner dimension of said housing in the vicinity of said weight member so as not to contact said housing during vibration of said elongated tubular member and of said weight member.

2. The dental scaler of claim 1, further comprising an elastomeric member at a forward end portion thereof, and an elastomeric member at a rearward end portion thereof which is more rearward than said weight member.

3. The dental scaler of claim 1, wherein said weight member is substantially disk-shaped, the disk-shaped weight member being arranged substantially transverse of said elongated tubular member.

4. The dental scaler of claim 1, further comprising anti-rotation means coupled to a forward end portion of said elongated tubular member for preventing rotation of said elongated tubular member relative to said housing.

5. The dental scaler of claim 4, wherein said anti-rotation means comprises an elongated member passing through an opening in a forward end portion of said elongated tubular member and resiliently connected to said housing at opposite ends of said elongated anti-rotation member.

6. The dental scaler of claim 5, wherein said elongated member of said anti-rotation means passes at least partially through an opening in said housing for preventing rotation relative to said housing.

7. The dental scaler of claim 1, comprising a rear resilient support means at said rearward end portion of said elongated tubular member for resiliently supporting said rearward end portion of said elongated tubular member relative to said housing, said weight member being located axially forward of said rear resilient support means along said elongated tubular member and said weight member not being connected to said rear resilient support means.

8. A vibration tool adapted to receive a working tool at an end thereof, and for imparting vibrations to the working tool at a stabilized frequency which remains substantially constant during use, comprising:
   an elongated housing having a forward end at which a working tool is removably connectable, and a rearward end including means for connection to a source of pressure working fluid;
   a substantially rigid elongated tubular member resiliently supported in said housing, said elongated tubular member having forward and rearward end portions;
   vibration means coupled to a portion of said elongated tubular member intermediate said forward and rearward end portions thereof, and driven by said pressure working fluid to vibrate said elongated tubular member, said vibration means including a rotor mounted on said elongated tubular member and two stop members on said elongated member close to said rotor on respective opposite sides of said rotor for limiting movement of said rotor in the longitudinal direction of said elongated tubular member;
   means at said forward end portion of said elongated tubular member for connecting a working tool thereto, said forward end portion of said elongated tubular member being vibrated by said vibration means to thereby impart vibration to said working tool;
   a weight member, separate from and spaced apart from said vibration means, and fixedly and immovably secured directly to a portion of said elongated tubular member spaced from the forward portion of said elongated tubular member without any resilient material between said weight member and said elongated tubular member, for stabilizing the frequency of the vibration imparted to said forward end portion of said elongated tubular member, at least a peripheral portion of said weight member having a space on both its sides in an axial direction of said tubular member so as to render said weight member substantially freely vibratable with said elongated tubular member, said weight member being located close to the rear end of said elongated tubular member and intermediate the position of said vibration means and a rearwardmost end of said elongated tubular member, and said weight member having an outer dimension smaller than the inner dimension of said housing in the vicinity of said weight member so as not to contact said housing during vibration of said elongated tubular member and of said weight member.

9. The vibration tool of claim 8, further comprising an elastomeric member at a forward end portion thereof, and an elastomeric member at a rearward end portion thereof which is more rearward than said weight member.

10. The dental scaler of claim 8, wherein said weight member is substantially disk-shaped, the disk-shaped weight member being arranged substantially transverse of said elongated tubular member.

11. The dental scaler of claim 8, further comprising anti-rotation means coupled to a forward end portion of said elongated tubular member for preventing rotation of said elongated tubular member relative to said housing.

12. The vibration tool of claim 11, wherein said anti-rotation means comprises an elongated member passing through an opening in a forward end portion of said elongated tubular member and resiliently connected to said housing at opposite ends of said elongated anti-rotation member.

13. The vibration tool of claim 12, wherein said elongated member of said anti-rotation means passes at least partially through an opening in said housing for preventing rotation relative to said housing.

14. The vibration tool of claim 8, comprising a forward resilient support means at said forward end portion of said elongated tubular member for resiliently supporting said forward end portion of said elongated tubular member relative to said housing, said weight member being located axially rearward of said forward resilient support means along said elongated tubular member and said weight member not being connected to said forward resilient support means.

* * * * *